(12) United States Patent
Ranganathan et al.

(10) Patent No.: US 6,350,879 B1
(45) Date of Patent: Feb. 26, 2002

(54) BENZISO-N (L-HISTIDINE METHYLESTER)-THIAZOLONE, PROCESS FOR THE PREPARATION THEREOF, AND USE THEREOF FOR RNA POLYMERASE INHIBITION

(75) Inventors: Subramania Ranganathan; Kannoth Manjheri Muraleedharan, both of Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/724,499

(22) Filed: Nov. 28, 2000

(51) Int. Cl.$^7$ .............................................. C07D 275/04
(52) U.S. Cl. ...................................................... 548/209
(58) Field of Search ......................................... 548/209

(56) References Cited

U.S. PATENT DOCUMENTS 3,642,836 A * 2/1972 Cusic et al. ................. 260/281

* cited by examiner

Primary Examiner—Laura L. Stockton
(74) Attorney, Agent, or Firm—Ladas & Parry

(57) ABSTRACT

The present invention discloses novel benziso-N(L-histidine methylester)-thiazolone compound of the formula 3 useful as a RNA polymerase inhibitor. These compounds are prepared by generating the free amine of the histidine methylester in situ by the addition of triethylamine to an ice cooled and stirred suspension of histidine methylester dihydrochloride in dry dichloromethane, adding dropwise, a dichloromethane solution of dithiodibenzoyl chloride and triethylamine to the said free amine at a temperature in the range of 0–5° C. to room temperature, stirring the reaction mixture for about 48 h, washing said reaction mixture with cold saturated NaHCO$_3$, subjecting it to a conventional organic-layer drying, followed by evaporating the solvent in vacuo, and eluting by chromatography the residue benziso-N(L-histidine methylester)-thiazolone.

4 Claims, 2 Drawing Sheets

BENZISO-N (L-HISTIDINE METHYLESTER)-THIAZOLONE, PROCESS FOR THE PREPARATION THEREOF, AND USE THEREOF FOR RNA POLYMERASE INHIBITION

FIELD OF THE INVENTION

The present invention relates to the compound benziso-N(L-histidine methylester)-thiazolone of the formula 3 and a process for the preparation thereof. More particularly, the present invention also relates to the use of compound of formula 3 for RNA polymerase inhibition by zinc ejection from [CCXX] boxes (C=cysteine, X=cysteine or histidine).

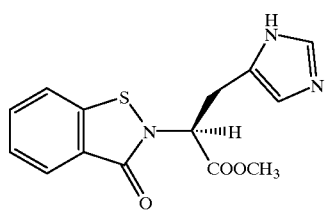

(3)

BACKGROUND OF THE INVENTION

The development of molecular systems, which can inhibit enzymes upon binding or by the removal of metal ions from the active sites, or similar pathways, have been recognized as an important strategy towards better drug candidates. Zinc plays a very important role in many enzymes/proteins, either by imparting stability to the conformation required for the biological function or by taking part in the catalytic process. Reference may be made to Lynne Regan (*Tibs*, 1995, 281–285) and J. M. Berg et.al (*J. Am. Chem. Soc.*, 1996, 118, 6514–6515), wherein the authors have found that the engineering of zinc finger domains in proteins could be used as a strategy for the modulation of its function and very recently, this approach has got enormous attention as a therapeutic tool for enzyme inhibition. Recent efforts in this domain have resulted in the identification of various reagents for zinc ejection from [CCXX] boxes, of which C-nitroso compounds (Rice, W. G.; Schaeffer, C. A.; Harten, B.; Villinger, F., South, T. L.; Summers, M. F.; Henderson, L. E.; Bess, J. W.; Arthur, L. O.; McDougall, J. S.; Orloff, S. L.; Mendeleyev, J.; Kun, E., Nature, 1993, 361, 473–475) and dithiobisbenzamides have got widespread recognition. The efficiency of dithiobisbenzamides in zinc ejection from nucleocapsid protein (NCp7) of HIV-1 has been studied in detail by Rice et. al. (Domagala, J. M.; Bader, J. P.; Gogliotti, R. D.; Sanchez, J. P. Stier, M. A.; Song, Y. Vara Prasad, J. V. N.; Tummino, P. J.; Scholten, J.; Harvey, P.; Holler, T.; Gracheck, S.; Hupe, D.; Rice, W. G.; Schultz, R. *Bioorganic and Medicinal Chemistry*, 1997, 5, 3, 569–579).

The drawback in the above-referred work is the disproportionation of dithiobisbenzamides under the biological conditions, which may give problems in developing these as ideal inhibitors. These chelators generally lack target specificity, which limits their applicability towards a specific zinc finger domain.

OBJECTS OF THE INVENTION

The main objective of the present invention is to introduce Benziso-N(L-histidine methylester)-thiazolone of the formula (3) as a new candidate for RNA polymerase inhibition by zinc ejection from [CCXX] boxes, which is synthesized as per the scheme shown in FIG. 1. The carboxylic group present in 3 (as ester) could be used for anchoring various recognition elements for increasing the target specificity.

Another objective of the present invention is to highlight the importance of the exchange mechanism depicted in FIG. 2 during the chelation process, which is supported by the high activity of this compound compared to the traditional chelators like ethylenediamine tetraacetic acid or o-phenanthroline.

An examination of the zinc finger domains present in proteins show the involvement of cysteine and histidine residues in the coordination process. This suggested a biomimetic approach in reagent design by crafting a histidine composite system with reducible S—N bond. We have successfully synthesized such a composite of formula (3) and demonstrated its efficiency in removing zinc by novel pathways envisaged in FIG. 2.

Recent advances in gene therapy necessitate the development of various agents that can interfere with information-function system at various levels. In this context, RNA polymerase, having subunit composition $\alpha_2\beta\beta'\sigma$ was selected for the exchange studies, because of its direct involvement in catalyzing transcription process—the first step in gene expression. Its $\beta'$ subunit is known to posses two zinc finger domains. The N-terminal domain is somewhat buried and metal ejection is not effective under normal conditions. Previous studies have shown that zinc present at the C-terminal location can be removed or exchanged readily, leading to a modified enzyme, which showed much reduced activity (Markov, D.; Naryshkina, T., Mustaev, A. and Severinov, K. *Genes & Development*, 1999, 13, 2439–2448.)

Our studies have shown that dithiobisbenzamides derived from amino acids having a proton source in the side chain (Serine, Threonine, Tryptophan, Histidine etc.) have a high tendency to be transformed to benzisothiazolones, compared to those with neutral pendant groups (eg. Alanine, Valine, etc.). Thus, reaction of dithiodibenzoyl chloride with Histidine methylester gave benzisothiazolone 3 as the sole product (FIG. 1) in 56% yield. It is proposed that the thiophenol liberated is oxidatively recycled to the dithiobisbenzamide, which would account for the observed yield, which otherwise would have been $\leq 50\%$.

In a typical experiment, the course of transcription of calf thymus DNA by *E. coli* RNA polymerase was monitored in the presence and absence of the redox system 3. The enzyme aliquot after admixing with 3 was incubated for 15 minutes and then dialyzed overnight. A general transcription assay was then carried out in a medium, which contained $^3$H UTP in addition to other nucleotides. The amount of radioactive UTP (uridine triphaspate) incorporated in the transcribed RNA was monitored by scintillation counter and the count, when compared to that obtained on using native enzyme gave the percentage loss of activity.

SUMMARY OF THE INVENTION

Figure 1:
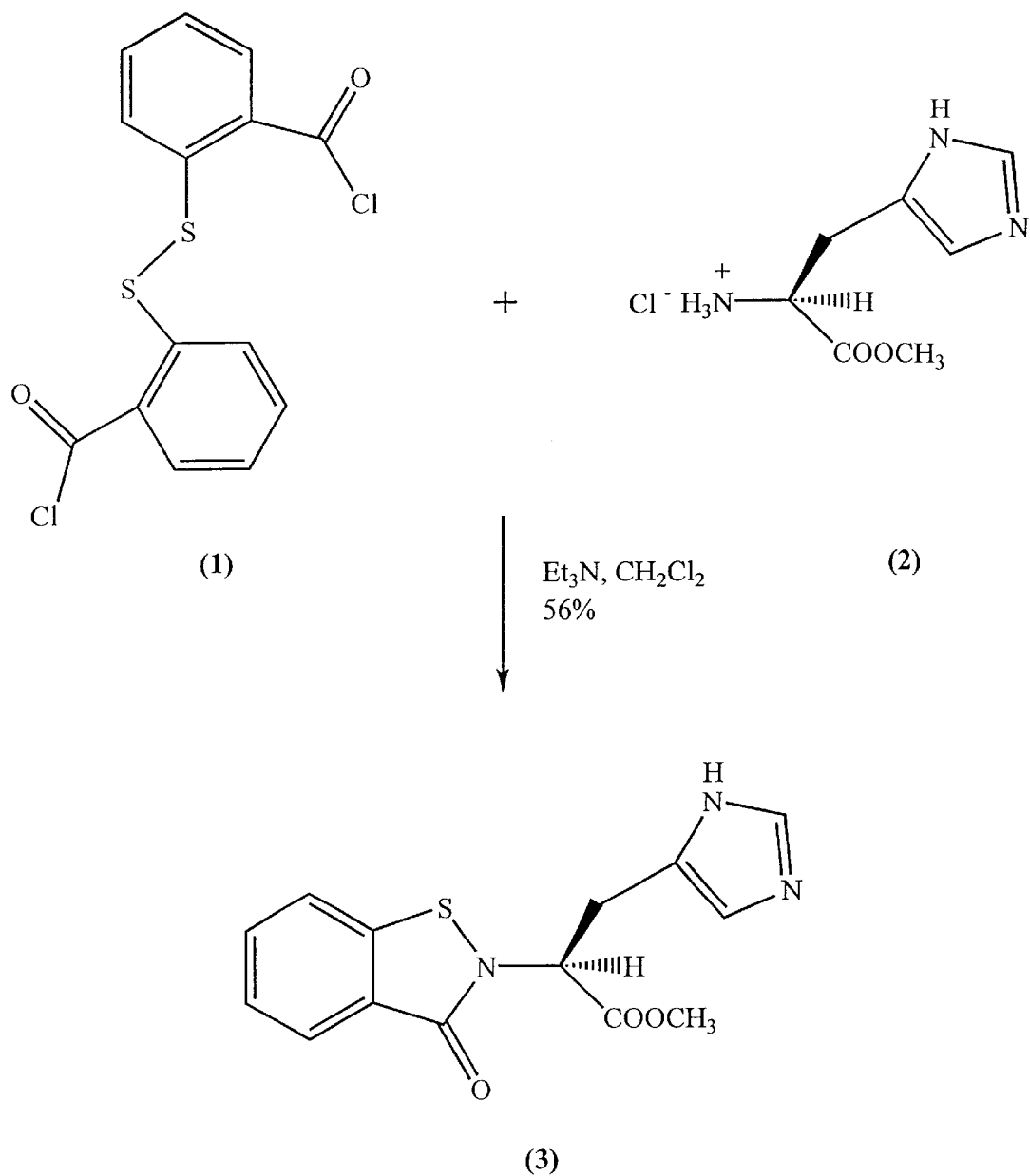
FIG. 1 shows the reaction of dithiodibenzoyl chloride with histidine methylester to obtain benziso-N(L-histidine methylester)-thiazolone.

The above and other objects of the present invention are achieved by providing Benziso-N(L-histidine methylester)- thiazolone of the formula (3) as a new candidate for RNA polymerase inhibition by zinc ejection from [CCXX] boxes, which is synthesized as per the scheme shown in FIG. 1. The carboxylic group present in compound 3 could be used for anchoring various recognition elements for increasing the target specificity.

Figure 2:
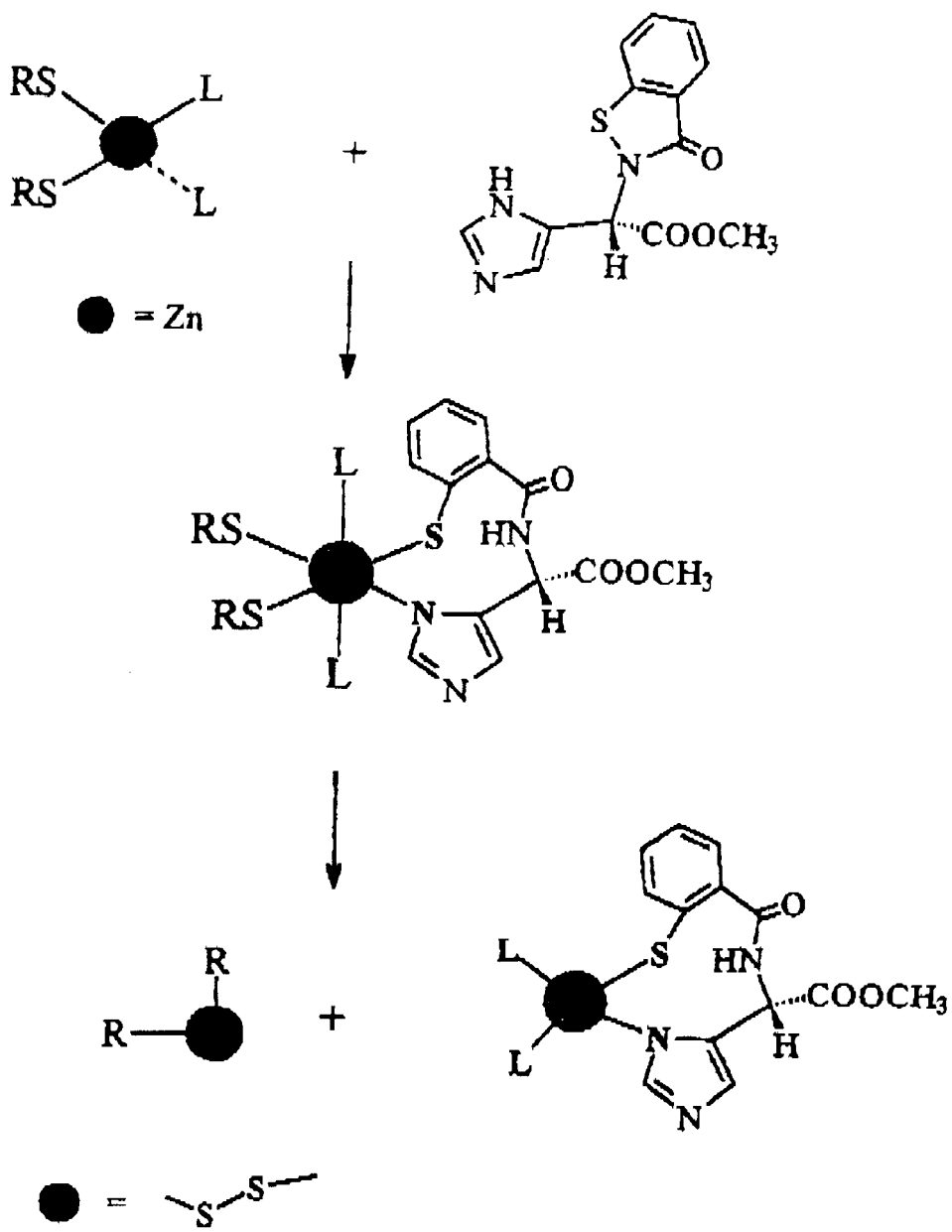
FIG. 2 represents the exchange mechanism for the removal of zinc.

The present invention also highlights the importance of the exchange mechanism depicted in FIG. 2 during the chelation process, which is supported by the high activity of this compound compared to the traditional chelators In the drawings accompanying this specification, FIG. 1 represents the synthetic route towards the preparation of benzisothiazolone 3, by treating dithiodibenzoyl chloride with histidine methyl ester and FIG. 2 represents the proposed mechanism which may be operating in the exchange process resulting in metal ejection from the active sites of enzymes.

Accordingly, the present invention provides novel benziso-N(L-histidine methylester)-thiazolone as new candidate for RNA polymerase inhibition by zinc ejection from [CCXX] boxes, wherein the compound is amino acid based and has a zinc finger prototype structure and is expected to undergo an exchange reaction during the chelation process as shown in FIG. 2.

The present also provides a process for the synthesis of Benziso-N(L-histidine methylester)-thiazolone of the formula 3 which comprises, a) generating the free amine of the histidine methylester in situ by the addition of triethylamine to an ice cooled and stirred suspension of histidine methylester dihydrochloride in dry dichloromethane b) adding dropwise, a dichloromethane solution of dithiodibenzoyl chloride and triethylamine to the said free amine at a temperature in the range of 0–5° C. to room temperature c) stirring the reaction mixture for about 48 h d) washing said reaction mixture with cold saturated NaHCO$_3$, e) subjecting it to a conventional organic-layer drying, followed by evaporating the solvent in vacuo, and f) eluting by chromatography the residue benziso-N(L-histidine methylester)-thiazolone using Hexane—Ethyl acetate as eluent.

In an embodiment of the present invention, the synthetic strategy towards Benziso-N(L-histidine methylester)-thiazolone, as a new candidate for RNA polymerase inhibition by removal of zinc from [CCXX] boxes is described, which is demonstrated by studying its inhibitory action on RNA polymerase, the key enzyme involved in gene expression using a radio isotope labelling assay.

The compounds of the present invention have 47% inhibition activity on RNA polymerase, the key enzyme involved in gene expression (47%). Their activity is 6250 times more than o-phenanthroline) and 12,500 times more than that of EDTA.

The following examples are given by way of illustration only and therefore should not be construed to limit the scope of the present invention.

EXAMPLE 1
Preparation of benzisothiazolone 3.

A solution of 2,2'-dithiodibenzoyl chloride (1) (1 g, 2.915 mmol) in dry CH$_2$Cl$_2$ (25 mL) and 0.9 mL (6.413 mmol) of triethylamine were simultaneously added dropwise to an ice cooled and stirred solution of the free amine of the histidine methyl ester [generated in situ by the addition of triethylamine (12.8 mmol) to an ice cooled and stirred suspension of histidine methyl ester dihydrochloride (2) (6.413 mmol) in dry CH$_2$Cl$_2$ (60 ml)]. The reaction was left stirred for 48 h at room temperature, washed with cold saturated NaHCO$_3$ (3×10 mL), the organic layer dried (MgSO$_4$), evaporated in vacuo and the residue chromatographed on silica gel using Hexane-EtOAc as eluent to afford 3.

Yield (56%); mp 240–242° C.; IR (KBr): 3446 (br), 3025, 1650, 1455, 1340; $^1$H NMR (CDCl$_3$-DMSO-d$_6$) δ 3.43 (m, 2H, CβH$_2$ merged with DMSO-d$_6$ water), 3.75 (s, 3H, COOCH$_3$), 5.62 (m, 1H, CαH), 6.73 (s, 1H, —N═CH), 7.38 (brs, 1H, imidazole NH), 7.48 (s, 1H, —C═CH), 7.64 & 7.94 (s, d, 4H, ArHs), FAB MS (m/z) (%): 304 (100%) (MH)$^+$.

EXAMPLE 2
RNA Polymerase Inhibition Studies with benzisothiazolone 3.

A mixture containing 0.8 μM solution of 3 (5 μL from 8 μM stock in methanol) and 0.4 μM of E. coli RNA polymerase (5 μl from 4 μM stock) in 1×transcription buffer $^a$ (5 μL) and 35 μL of milliQ water was incubated for 15 min, and dialysed $^b$ overnight, 4×Transcription assay mixture $^c$ (10 μL) was diluted with 10 μL of milliQ water and admixed with 20 μL of treated and dialyzed enzyme. The mixture was incubated for 20 minutes and spotted on to a DE81 filter paper strip $^d$, which was pre-coated with EDTA to arrest further transcription. The filter paper strips were allowed to air dry for three hours, washed successively with 5% Na$_2$HPO$_4$ solution (3×200 mL, 10 min. each), distilled water (2×200 mL, 5 min. each) and then with ethanol (2×75 mL). The strips were then dried under an IR lamp, put in the scintillation fluid and noted the count in the scintillation counter. The count given by the native enzyme was taken as 100% and the relative value shown by the inhibited enzyme gave the percentage loss of activity. The reagent treated enzyme showed only 53% activity compared to the native enzyme, thus showing a 47% inhibition of activity by the compound 3.

Notes a. Composition of the 1×Transcription buffer:
50 mM Tris.HCl [tris=tris(hydroxymethyl)methylamine] (pH 7.8); 0.1 mM EDTA (ethylenediamine tetraacetic acid); 0.1 mM DTT (dithiothreitol); 50 mM NaCl; 3 mM Mg(OAc)$_2$;BSA (bovine serum albumine) 25 mg/mL.

b. Dialysis i) Preparation of the dialysis tubings: Small pieces of dialysis tubing (10–20 cm, 10 nos.) were boiled in 250 mL of 2% NaHCO$_3$ solution for 10 min. They were then washed thoroughly with distilled water (4×100 mL) and again boiled for 10 min. in distilled water (200 mL), allowed to cool and stored at 5° C.

ii) Composition of the dialysis buffer 10 mM Tris.HCl (pH 8), Glycerol 5% (v/v); 0.1 mM EDTA; 0.1 mM DTT; 50 mM NaCl.

c. Composition of the 1×Transcription assay mixture: 40 mM Tris.HCl (pH 8); 10 mM MgCl$_2$; 1 mM EDTA; 16 mM βME (β-mercaptoethanol) 0.2 mM ATP (adenosine triphosphate); 0.2 mM CTP (cytidine triphospate); 0.2 mM GTP (guanosine triphospate); 0.05 mM UTP (uridine triphospate); 50 mM $^3$H UTP, Calf thymus DNA, 1 mg/mL. The solution was made up using milliQ water.

d. DE81 filter paper strips were cut in 4×4 cm size, numbered at the corner using HB pencil and 100 μL of 50 mM EDTA solution was spotted on this. Gloves and forceps were used while handling. They were allowed to air dry.

The main advantages of the present invention are:

1. The compound 3 is amino acid based and hence the bio-degradation products may not be harmful to the body, which makes it pharmacologically more attractive.
2. The carboxylic group present in 3 (as ester) could be used for anchoring various recognition elements for increasing the target specificity.
3. The compound 3 is stable at normal conditions.

REFERENCES

1. Lynne Regan, *Tibs*, 1995, 281–285.
2. Rice, W. G.; Schaeffer, C. A.; Harten, B.; Villinger, F; South, T. L., Summers, M. F; Henderson, L. E. Bess, J. W.; Arthur, L. O. McDougall, J. S., Orloff, S. L., Mendeleyev, J.; Kun, E., Nature 1993, 361, 473–475.
3. a) Domagala, J. M.; Bader, J. P.; Gogliotti, R. D.; Sanchez, J. P.; Stier, M. A.; Song, Y; Vara Prasad, J. V. N.; Tummino, P. J.; Scholten, J.; Harvey, P.; Holler, T., Gracheck, S.; Hupe, D.; Rice, W. G.; Schultz, R. *Bioorganic and Medicinal Chemistry*, 1997, 5, 3, 569–579. b) Tummino, P. J., Scholten, J. D.; Harvey, P. J.; Holler, T. P., Maloney, L.; Gagliotti, R.; Domagala, J., Hupe, D. *Proc. Natl. Acad. Sci. USA*, 1996, 93, 969–973.
4. Markov, D.; Naryshkina, T.; Mustaev, A. and Severinov, K. *Genes & Development*, 1999,13,2439–2448.

What is claimed is:

1. Benziso-N(L-histidine methylester)-thiazolone compound of the formula 3

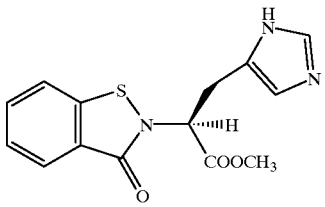

(3)

useful as a RNA polymerase inhibitor.

2. A process for the synthesis of Benziso-N(L-histidine methylester)thiazolone of the formula

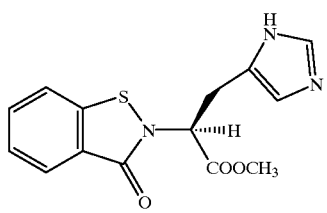

(3)

which comprises,
(a) generating the free amine of the histidine methylester in situ by addition of triethylamine to an ice cooled and stirred suspension of histidine methylester dihydrochloride in dry dichloromethane,
(b) adding dropwise, a dichloromethane solution of dithiodibenzoyl chloride and triethylamine to the free amine at a temperature in the range of 0–5° C. to room temperature,
(c) stirring the reaction mixture for about 48 hours,
(d) washing said reaction mixture with cold saturated NaHCO$_3$,
(e) subjecting the reaction mixture of step (d) to organic-layer drying, followed by evaporating the solvent in vacuo, and
(f) eluting by chromatography the residue benziso-N(L-histidine methylester)-thiazolone using hexane-ethyl acetate as eluent.

3. A method for inhibiting RNA polymerase in a subject comprising administering to the subject An amount of Benziso-Z(L-histidine methylester)-thiazolone of formula 3

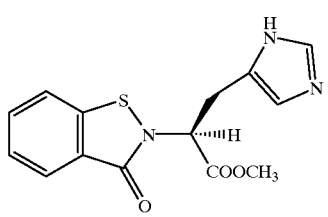

(3)

effective to inhibit RNA polymerase.

4. A method as claimed in claim 3 wherein the Benziso-N(L-histidine methylester)-thiazolone of the formula 3 inhibits RNA polymerase by zinc ejection from the [CCXX] boxes.

* * * * *